(12) United States Patent
Mayer et al.

(10) Patent No.: US 10,058,412 B2
(45) Date of Patent: Aug. 28, 2018

(54) IMPLANT, METHOD OF PREPARING AN IMPLANT, IMPLANTATION METHOD, AND KIT OF PARTS

(71) Applicant: WOODWELDING AG, Stansstad (CH)

(72) Inventors: Jörg Mayer, Niederlenz (CH); Andrea Muller, Winterthur (CH); Peter Brunner, Muri bei Bern (CH)

(73) Assignee: WOODWELDING AG, Stansstad (CH)

( * ) Notice: Subject to any disclaimer, the term of this patent is extended or adjusted under 35 U.S.C. 154(b) by 845 days.

(21) Appl. No.: 14/492,837

(22) Filed: Sep. 22, 2014

(65) Prior Publication Data

US 2015/0012091 A1 Jan. 8, 2015

Related U.S. Application Data

(60) Division of application No. 12/486,470, filed on Jun. 17, 2009, now Pat. No. 8,870,572, which is a
(Continued)

(51) Int. Cl.
*A61C 17/00* (2006.01)
*A61F 2/02* (2006.01)
(Continued)

(52) U.S. Cl.
CPC ............... *A61F 2/02* (2013.01); *A61B 17/68* (2013.01); *A61C 8/0012* (2013.01);
(Continued)

(58) Field of Classification Search
CPC .............. A61B 18/68; A61B 17/00491; A61B 17/0401; A61B 2017/005; A61C 8/0012;
(Continued)

(56) References Cited

U.S. PATENT DOCUMENTS 3,642,346 A  2/1972  Dittmar
3,966,520 A  6/1976  Fallenbeck et al.
(Continued)

FOREIGN PATENT DOCUMENTS

EP  1688101  2/2005
GB  2045082  10/1980
(Continued)

*Primary Examiner* — Cris L Rodriguez
*Assistant Examiner* — Mirayda A Aponte
(74) *Attorney, Agent, or Firm* — Rankin, Hill & Clark LLP (57) ABSTRACT

An implant includes first thermoplastic material portions, and second thermoplastic material portions liquefiable by mechanical vibrations and being in contact with the first thermoplastic material portions, wherein the second thermoplastic material portions preferably constitute at least a part of a surface of the implant, and wherein the first thermoplastic material portions have a glass transition temperature above an implantation temperature (about 20° C. to 40° C.), and wherein the second thermoplastic material portions either have a glass transition temperature below the implantation temperature or are able to transform non-mechanical energy into heat.

19 Claims, 5 Drawing Sheets

Related U.S. Application Data continuation-in-part of application No. PCT/CH2008/000043, filed on Feb. 5, 2008.

(60) Provisional application No. 60/888,798, filed on Feb. 8, 2007.

(51) Int. Cl.

| | | |
|---|---|---|
| *A61B 17/68* | (2006.01) | |
| *A61C 8/00* | (2006.01) | |
| *A61B 17/00* | (2006.01) | |
| *A61B 17/04* | (2006.01) | |
| *A61F 2/08* | (2006.01) | |
| *A61F 2/28* | (2006.01) | |
| *A61F 2/30* | (2006.01) | |
| *A61F 2/44* | (2006.01) | |
| *A61F 2/46* | (2006.01) | |

(52) U.S. Cl.
CPC ...... *A61C 8/0016* (2013.01); *A61B 17/00491* (2013.01); *A61B 17/0401* (2013.01); *A61B 2017/005* (2013.01); *A61F 2/0811* (2013.01); *A61F 2/28* (2013.01); *A61F 2/30* (2013.01); *A61F 2/30749* (2013.01); *A61F 2/442* (2013.01); *A61F 2002/30065* (2013.01); *A61F 2002/4683* (2013.01); *A61F 2210/0071* (2013.01); *A61F 2220/0008* (2013.01)

(58) Field of Classification Search
CPC .......... A61C 8/006; A61F 2/0811; A61F 2/28; A61F 2/30; A61F 2/30749; A61F 2/442; A61F 2002/30065; A61F 2210/0071; A61F 2210/0008

USPC ....................... 433/172–176, 201.1
See application file for complete search history.

(56) References Cited

U.S. PATENT DOCUMENTS

| | | | |
|---|---|---|---|
| 4,778,474 | A | 10/1988 | Homsy |
| 4,904,534 | A | 2/1990 | Nagai |
| 4,955,540 | A | 9/1990 | Fuller et al. |
| 5,037,442 | A | 8/1991 | Wintermantel et al. |
| 6,001,201 | A | 12/1999 | Vincent et al. |
| 6,080,161 | A | 6/2000 | Eaves, III et al. |
| 6,913,666 | B1 | 7/2005 | Aeschlimann et al. |
| 6,921,264 | B2 | 7/2005 | Mayer et al. |
| 7,008,226 | B2 | 3/2006 | Mayer et al. |
| 7,335,205 | B2 | 2/2008 | Aeschlimann et al. |
| 7,967,820 | B2 | 6/2011 | Bonutti et al. |
| 8,357,201 | B2 | 1/2013 | Mayer et al. |
| 2005/0249773 | A1 | 11/2005 | Maspero et al. |
| 2007/0270833 | A1* | 11/2007 | Bonutti .............. A61B 17/0401 606/28 |
| 2009/0131947 | A1 | 5/2009 | Aeschlimann et al. |
| 2010/0036441 | A1 | 2/2010 | Procter |
| 2010/0274358 | A1* | 10/2010 | Mueller .............. A61B 17/7059 623/17.16 |
| 2011/0208310 | A1 | 8/2011 | Aschmann et al. |
| 2011/0295253 | A1 | 12/2011 | Bonutti et al. |

FOREIGN PATENT DOCUMENTS

| | | |
|---|---|---|
| WO | 02/069817 | 9/2002 |
| WO | 2004/017927 | 3/2004 |
| WO | 2005/079696 | 9/2005 |

* cited by examiner

IMPLANT, METHOD OF PREPARING AN IMPLANT, IMPLANTATION METHOD, AND KIT OF PARTS

CROSS REFERENCE TO RELATED APPLICATION

This application is a divisional of U.S. Ser. No. 12/486,470, filed Jun. 17, 2009, which is a continuation-in-part of PCT Application No. PCT/CH2008/000043, filed on Feb. 5, 2008, designating the United States and which also claims priority to U.S. Provisional Application 60/888,798 filed on Feb. 8, 2007.

BACKGROUND OF THE INVENTION

Field of the Invention

The invention lies in the field of medical technology or dentistry and relates to an implant and to a method of preparing an implant for implantation. It further relates to a kit of parts for carrying out the method and to an implantation method. The implant according to the invention is suitable for being implanted in human or animal tissue, in particular in hard tissue such as bone, but it is also suitable for being fixed in a natural tooth, i.e. to a dentine or enamel surface. Although in the latter case one skilled in the art would not refer to an "implant" and to "implantation method", these terms are used in the following as including elements and methods suitable for endodontic use.

Description of Related Art

In WO 02/069 817, a method of implanting an implant in human or animal tissue has been disclosed. The implant includes surface regions of a material liquefiable by mechanical vibration. The liquefiable material is in contact or can be brought into contact with the tissue part in a region in which the tissue part has surface unevennesses or openings or in which such surface unevenesses or openings can be created by hydrostatic pressure. The implant is then impinged with mechanical vibration and simultaneously pressed against the tissue part until at least a part of the liquefiable material is liquefied and is pressed into said surface unevennesses or openings. Thereafter, the liquefiable material is let to re-solidify, while the implant is still pressed against the tissue part. WO-04/017927 discloses a similar method for fixing elements, e.g. fillings or root pins, in parts of natural teeth.

The basic principle of the above named methods has been proven to be successful in surgery and dentistry, especially for fixing an implant in bone tissue or a corresponding element in the dentine or enamel of a tooth. The liquefiable material—often being a thermoplastic—after re-solidification, provides substantial primary stability of the connection between the implant and the bone tissue.

In order to provide sufficient conductivity of mechanical vibration energy from a proximal to a distal end of the implant and to achieve a sufficient primary stability, the liquefiable thermoplastic material has to be of a certain minimal stiffness. Generally, the modulus of elasticity (Young's modulus) should be 0.5 GPa or higher. A not too low modulus of elasticity is also necessary for the mechanical vibrations to be conducted through the thermoplastic material to the surface portion which is in contact with the tissue. However, a high modulus of elasticity adversely affects the thermoplastic material's capability of absorbing mechanical energy (absorptivity). More concretely, the absorptivity is proportional to the square of the strain induced in the material by the mechanical vibration, which strain for a given power is the higher, the softer the material. Therefore, for materials with a high modulus of elasticity the local friction between the vibrating thermoplastic material and the tissue plays an important role in the liquefying process.

However, for implanting into soft or brittle tissue—such as osteoporotic bone tissue—it is hardly possible to exploit such friction, since it is not possible to excerpt the necessary force to the tissue. The possible frictional force is also limited by the contact area between tissue and implant surface, which contact area is reduced for spongy tissue with large cavities in the tissue material.

BRIEF SUMMARY OF THE INVENTION

It is an object of this invention to provide an implant (or element for endodontic use) and methods of implanting an implant and of preparing an implant, which overcome drawbacks of prior art implants and methods. It is also an object of the invention to provide an implant and a method of implanting an implant by means of mechanical vibration, which method provides a high primary stability of the connection to the tissue it is implanted in. The implant should also be suited for soft, spongy and/or brittle tissue and for implantation with little force.

The method and implant according to a first aspect of the invention make use of the concept that the implant includes portions of thermoplastic material, preferably in the vicinity of a surface, which material portions are above their glass transition point when the mechanical vibrations act and therefore have a high absorptivity for mechanical energy. In addition, the implant includes thermoplastic material portions which are located adjacent to the above named material portions and which do not have a high absorptivity for mechanical energy. These material portions may include portions of a thermoplastic material that at the onset of the mechanical vibrations are below the glass transition temperature, but which are all the same liquefiable by the mechanical vibrations. These additional material portions have a higher modulus of elasticity and thereby bring about a good transport of mechanical energy to the contact surfaces and also add to the stability of the implant and its connection to the tissue.

The approach according to the first aspect of the invention provides a way out of the dilemma that the thermoplastic on the one hand should have a high modulus of elasticity to be a good enough conductor for the sound or ultrasound waves (mechanical vibrations), and on the other hand should be a good absorbent for the very same sound waves.

The absorption of mechanical energy in a vibrating body is proportional to the square of the mechanical strain times the quantity $\tan(\delta)$, which is the quotient between the imaginary (dissipative) part $E''$ of the complex mechanical modulus $E^*=E'+iE''$ and its real (elastic) part $E'$. The real part of the complex mechanical modulus is also called storage modulus and for low frequencies corresponds to Young's modulus of elasticity. The imaginary part is also called loss modulus and is indicative of the viscous behavior. The angle $\delta$ corresponds to the phase difference of the stress acting on the solid and the strain.

Above the glass transition temperature, the storage modulus is lower, compared to temperatures below the glass transition temperature, by orders of magnitude, and therefore for a given stress acting on the solid—and also for a given vibration energy coupled into the solid—the strain, i.e. the mechanical deflection, increases drastically. Therefore, the absorbed energy also increases drastically above the glass transition temperature. The quantity tan(δ) is at a maximum at the glass transition temperature (some even define the glass temperature as the temperature where tan(δ) is at a maximum) and in general is higher for temperatures clearly above the glass transition temperature than for temperatures below it, so that the dependence of the energy absorption on tan(δ) also contributes to the enhanced absorptivity above the glass transition point.

The material regions which are above the glass transition temperature, when the mechanical vibrations start acting, are capable to serve as a kind of heater for adjacent thermoplastic material portions which are, when the vibrations start acting, below the glass transition temperature. Therefore, not only the highly energy absorptive (second) material portions are liquefied more easily, but also adjacent (first) material portions of the "harder", initially less absorptive thermoplastic material are liquefied more easily due to the heating effect by the second material. This effect is enhanced, if the "harder", first thermoplastic material, which is initially less absorptive, has a glass transition temperature not too far above an implantation or body temperature (e.g. about 37° C.), i.e. a glass transition temperature of e.g. between 37° C. and 150° C. In this case, portions of the first material which by being situated adjacent the second material are heated above the glass transition temperature by the second material, and therewith get an enhanced absorptivity also. This means that the portions of the second material can be very small. They may be viewed as decreasing the activation energy for liquefaction of the "harder" first material portions, thus as a kind of "catalyst". Preferably the second material portions are small compared with the volume of the implant or of the first material portions such that the less advantageous mechanical properties of this second material, if they are not wearing off, see further below, have only a minor effect on the mechanical stability of the connection between implant and bone.

In accordance with the prior art, an enhanced transformation of mechanical energy into heat at the places where the thermoplastic material was to melt, for example, had to be achieved by a high contact pressure between the implant and the adjacent tissue (and a resulting higher friction). This is not possible if the tissue is soft or brittle or the contact surface is small. The approach according to the invention differs therefrom in that material portions in the vicinity of the surface are itself in a state, or brought into a state, in which its material properties cause an enhanced absorption of mechanical energy and transformation thereof into heat. Therefore, according to the first aspect of the invention there are, at the onset of the mechanical vibrations, the material portions with an enhanced absorptivity being independent of the shape of the implant and independent of contact forces. Preferably, these material portions would melt when vibrated even if they were not in contact with any tissue and of course even more so when in contact with the tissue.

The effect described above enables implantation with only small forces applied to the implant, and therefore implantation e.g. in brittle bone tissue. The implantation method, in general, is especially suited for implantation in tissue (bone, dentine, enamel, but also tendon or ligament or cartilage, meniscal tissue), even if these tissues cannot be subjected to large external forces.

The effect of the implant comprising, e.g. in the vicinity of its surface, material portions which are above their glass transition point when the mechanical vibrations act or start acting, can be achieved in one (or both) of the following ways:

The implant comprises second thermoplastic material portions, preferably along a surface region of the implant, which second thermoplastic material portions are, at an implantation temperature, above the glass transition point. In addition, the implant comprises first material portions which are also liquefiable by mechanical vibration but have a glass transition temperature higher than the implantation temperature, i.e. are below the glass transition point when the mechanical vibrations start, wherein the first and second material portions are situated adjacent to each other.

The implant comprises second (preferably thermoplastic) material portions, preferably along a surface region of the implant, which second material portions are capable of absorbing non-mechanical energy. In addition, the implant comprises first material portions fulfilling the same conditions as discussed under A and furthermore being capable of conducting the non-mechanical energy from a proximal end thereof to the second material portions, wherein the first and second material portions are arranged adjacent to each other.

In both cases named above, the implant may include, in addition to the first and second material portions, further material portions of any (thermoplastic or not thermoplastic) material. Such further material portions may, for example, be a core or a sleeve including one or more holes, which sleeve contains the thermoplastic material. Other embodiments of such further material portions for functions different from a core or sleeve function can be envisaged.

In both cases named above, the thermoplastic material portions need not be—though in many embodiments they preferably are—generally thermoplastic. Rather, they may be of a thermosetting type and be, on implantation, in a not cross-linked or not completely cross-linked state in which they have thermoplastic properties. After implantation, they are then preferably cross-linked.

In the case of group A, the second material portions may be produced by a local modification in surface regions (which may cover the entire surface) of the first thermoplastic material having without the modification a glass transition temperature above the implantation temperature and by the modification becoming a "softer" thermoplastic material with a glass transition temperature below the implantation temperature. Such modification can be achieved e.g. by a plasticizing agent, e.g. a substance with a plasticizing effect which substance may diffuse out of the implant after implantation. In the following text, such modification of a thermoplastic material in the vicinity of surface regions (which may optionally cover the entire implant surface) is called "a method of preparing an implant for implantation".

Alternatively, the second material portions are made of a different thermoplastic material (comprising a different polymeric composition, i.e. different molecule chains) than the first thermoplastic material. The second material portions may form a locally confined or entire coating of the first thermoplastic material, for example of a thickness between 0.05 mm and 2 mm, preferably between 0.1 mm and 0.5 mm. The second material portions may also have the shape of edges or tips protruding from the first material regions and then have larger dimensions. As discussed above, the second thermoplastic material portions may include a substance with a plasticizing effect which substance may diffuse out of the implant after implantation.

The implantation temperature may be a temperature between 20° and a body temperature (e.g. 37° to 40° C.). In many cases, the implantation temperature is 37° or a temperature between 35° and 38°. However, there may be surgical operations in which the tissue temperature falls to a temperature clearly below 37°, or where some parts are assembled ex situ, so that the implantation temperature may be accordingly lower. In the following description, the implantation temperature is mostly assumed to be a body temperature, i.e. a temperature in the region of 37°. It goes without saying that the teaching of the description is readily adaptable to another implantation temperature.

Embodiments of group B include an absorber capable of absorbing non-mechanical energy conducted through a central region (the first material portions). Such an absorber is a means for selectively absorbing incident energy at the surface where liquefaction is to start or to occur. As an alternative to the above-described way of causing the surface portions to be liquefied by the impact of mechanical vibrations impinging after the and/or simultaneously with the non-mechanical energy, the energy of the non-mechanical energy may also be chosen to be sufficient to liquefy thermoplastic material portions at the surface.

For special embodiments of group B, the source of non-mechanical energy is a radiation source—especially a laser radiating in the infrared or visible part of the optical spectrum—and the absorber is a radiation absorber, such as a particulate or molecular absorber embedded in the transparent thermoplastic material of the peripheral region or contained in pores thereof or such as an absorbing body adjacent to the transparent thermoplastic material.

An according implant comprises an implant body, the implant body having a central region and a peripheral region, the central region including a material transparent for electromagnetic radiation of a spectral range, the spectral range being part of at least one of the infrared part of the optical spectrum and of the visible part of the optical spectrum, the peripheral region including a thermoplastic material and an absorber capable of absorbing electromagnetic radiation of the spectral range, the absorber being in immediate contact with thermoplastic material of the peripheral region, wherein the central region is capable of conducting electromagnetic radiation coupled in from the proximal end to the peripheral region.

A method of implanting such an implant in human or animal tissue, includes the steps of:

providing the implant, the implant comprising an implant body with a central region and a peripheral region, the central region comprising material transparent for electromagnetic radiation of a spectral range, the spectral range being part of at least one of the infrared part of the optical spectrum and of the visible part of the optical spectrum, the peripheral region comprising a thermoplastic material and an absorber capable of absorbing electromagnetic radiation of the spectral range;

coupling electromagnetic radiation that includes radiation within the spectral range into the implant body from the proximal end thereof, the electromagnetic radiation being conducted through the central region and being at least partially absorbed by the absorber;

causing thermoplastic material portions in the peripheral region to be liquefied, and pressing the liquefied thermoplastic material portions into at least one of surface unevenness, pores, and of surface inhomogeneities of the tissue; and letting the thermoplastic material portions re-solidify to yield an anchor of the implant.

According to another aspect of the invention, the implant includes thermoplastic material portions of a glass transition temperature below the implantation temperature, which material portions preferably form at least a part of the implant surface and which material portions include a polymer and a plasticizing agent. The plasticizing agent is such that its effect wears off with a time constant that is lower than a time constant of resorption of resorbable polymers by at least an order of magnitude, preferably with a time constant of at the most a few days (such as a week or less, preferably one day or less). For example, the plasticizing agent may be a plasticizer, i.e. a substance having a platicizing effect. After implantation, the plasticizer is to diffuse out of the implant with a time constant that is lower than the time constant of resorption of resorbable polymers by at least an order of magnitude, preferably with a time constant of at most a few days (such as a week or less, preferably one day or less). Preferably, the plasticizer is resorbable or excretable.

After the plasticizing agents' effect has worn off, the remaining polymer preferably has a glass transition temperature of above the implantation temperature and therewith mechanical properties suitable for a stable connection between the tissue and the implant.

As an alternative to the plasticizing agent being a plasticizer (a substance), the plasticizing agent may have the form of thermal energy, being introduced by other means than mechanical vibration or friction, e.g. by light, by contact (hot water bath or the like), by microwave, etc. either from an inside to an outside or from an outside to an inside. The wearing off would then be due to heat diffusion.

By the approach according to the second aspect of the invention, a relatively "soft", easily liquefiable polymer material is used for the implantation process and thus is especially suited for anchoring in soft and/or brittle tissue. Thereafter, by way of the plasticizing agent being removed, the polymer material hardens, whereby the connection is further strengthened.

The implant according to the second aspect also includes "harder" material portions which have a modulus of elasticity of 0.5 GPa or higher and which ensure a sufficient transport if mechanical energy from a proximal end towards a distal end of the implant. These material portions may consist of non-liquefiable material(s), such as titanium, ceramic, a thermosetting polymer etc.

These "harder" material portions, however, may as an alternative include or even consist of material portions of a first thermoplastic material which is also liquefiable by mechanical oscillations but which has a glass transition temperature of above the implantation temperature. Such first thermoplastic material portions are preferably in contact with the "soft" (second) thermoplastic material portions. In this case, the first and second aspects of the invention are combined to an especially advantageous embodiment.

The "harder" material portions, since they are advantageous for transporting the mechanical energy, may reach from the proximal end of the implant to the distal end of the implant or to only a short distance (for example 5 mm or less or even 1 mm or less) therefrom.

According to a yet another aspect of the invention, in a variant of the first aspect, the implant comprises a first portion of thermoplastic material and comprises a second portion of thermoplastic material, the latter preferably in the vicinity to a surface. The second portion is made of a thermoplastic foam with open or closed pores. The first portion may be made of a same thermoplastic material as the material of the second portion, or of a different thermoplastic material.

The structure of a foam has the following impact on the properties of the implant when the mechanical vibrations act upon the implant: At the interface (which may be a clear boundary or may be gradual) between the first and the second portions, the pressure is concentrated from the full cross section surface to the smaller cross section of the material in the first, porous region. In other words, the foam structure functions like an interior energy concentrator. Therefore, the second portion(s) is/are heated, by absorption of the mechanical energy, more efficiently than the first portion, and is/are for example liquefied before the latter. Much like in the invention according to its first aspect, the second portion may serve as a kind of heater for adjacent thermoplastic material of the first portion. Also in accordance with this third aspect, the first portion material may be chosen so as to be brought above its glass transition temperature by the second portion heating effect. Other considerations applied to the first aspect above, apply mutatis mutandis for the third aspect.

In the second material portion, the pore size of closed pores is, for example, between 0.2-200 µm, preferably between 10-50 µm. If the second material portions contain open pores, the pore size may be in a broad range, for example ranging from 0.1 µm to 200 µm. Especially preferred—for reasons explained below—are pore sizes smaller than 50 µm, preferably smaller than 5 µm, especially preferred between 0.1 µm and 1 µm.

Methods for creating porosity materials are for example described in F. A. Maspero, "Biodegradable, open porous scaffolds for the prevention of alveolar bone loss after tooth extraction", PHD Thesis ETH Zürich, No. 14270, 2002.

Different aspects of the invention bring about the advantage that by a chosen arrangement of first and second material portions, or by a chosen concentration profile of a plasticizer, or other means of bringing thermoplastic material above its glass transition temperature, it is possible to define regions where the implant, when subject to the mechanical energy, starts liquefying. This may even be independent of the quality of adjacent tissue and may even be independent on contact forces etc. Therefore, the approach according to the invention brings about the advantage of supporting implantation in situations where no or almost no contact force can be applied, where the tissue is very weak, where the liquefiable material is to be melted at places not in contact with hard tissue/hard tissue replacement material (for example in a 'blind rivet' fashion) etc. This applies both, to otherwise conventional, pin-like implants and forward implantation, and to newly developed implants/implantation methods, as for example described in patent applications PCT/CH 2007/000459 (based on 60/826, 300), and U.S. 60/983,791, all incorporated herein by reference.

According to a special embodiment, therefore, the implants and methods described herein, referring to any aspect or combination of aspects of the invention, are especially suited in combination with:

A method for producing an anchorage in a load bearing tissue, the anchorage having a load bearing capability and being created with the aid of mechanical vibration and a thermoplastic material which is liquefiable by the mechanical vibration, the method including the steps of:

providing a vibrating element with a distal end and a proximal end, wherein the proximal end is rigidly attached to a vibration source and the vibrating element is capable of transmitting vibration of the vibration source to the distal end and wherein the distal end includes a contact face, providing a counter element with a contact end and an opposite end, wherein the contact end includes a second contact face being adapted to the first contact face to be able to be positioned against the first contact face, providing the liquefiable thermoplastic material on at least one of the first and second contact faces, positioning the vibrating element and the counter element relative to said tissue, while holding the elements against each other with first and second contact faces in contact with each other, and with one of a pair of opposite holding forces being applied to each one of said elements, such that a tissue surface extends across outer edges of the contact faces, vibrating the vibrating element while holding the elements against each other and thereby liquefying the liquefiable thermoplastic material between the contact faces, maintaining the vibration and the holding forces and thereby moving the elements against each other and letting the liquefied material flow out from between the contact faces for a period of time sufficient for the liquefied material to contact the tissue surface and, on re-solidification, to form a positive fit connection between at least one of the elements and the tissue surface.

In this, the (second) more easily liquefiably material portions (according to either one or combination of the aspects of the invention) of liquefiable material may constitute the liquefiable material at at least one of the first and the second contact face, or may constitute a portion thereof—for example at a place where enhanced liquefaction is desired —, and/or it may be present at a location different from the contact faces to further liquefaction at such locations different from the contact faces.

The invention, as a further consequence, also relates to a device for producing an anchorage in a load-bearing tissue with the aid of mechanical vibration and a thermoplastic material which is liquefiable by the mechanical vibration, the device including:

a vibrating element with a distal end and a proximal end, the vibrating element being capable of transmitting vibration from its proximal end to its distal end, and wherein the distal end includes a contact face, a counter element with a contact end and an opposite end, wherein the contact end includes a second contact face being adapted to the first contact face to be able to be positioned against the first contact face, wherein the liquefiable thermoplastic material is located on at least one of the first and second contact faces, and wherein, when the contact faces are positioned against each other, either the vibrating element is able to reach past or through the counter element or the counter element is able to reach past or through at least the distal end of the vibrating element. Also in this, the (second) more easily liquefiably material portions (according to either one or a combination of the aspects of the invention) of liquefiable material may constitute the liquefiable material at at least one of the first and the second contact face, or may constitute a portion thereof—for example at a place where enhanced liquefaction is desired —, and/or it may be present at a location different from the contact faces to further liquefaction at such locations different from the contact faces. Also, either the vibrating element or the counter element or the assembly of both may be an implant according to any one of the aspects of the invention.

Concerning possible designs and set-ups, it is referred to U.S. 60/983,791, especially to FIG. 2 and FIG. 13, (and variants in FIGS. 3-5; and in FIGS. 14-16), in FIGS. 17/18 (variants in FIGS. 19-21), and in FIG. 22, as well as the description of these figures, the discussion of the underlying principles and the according dependent claims. In these such set-ups and designs are described in detail.

Also PCT/CH 2007/000459 describes implants and set-ups where certain regions of the implant are especially destined to be liquefied, and a combination of the approach according to the invention is beneficial. Especially, in contact faces and/or peripheral regions in accordance with either aspect or combination of aspects of the present invention, there may be a material portion that is more easily liquefiable. Especially all of the FIGS. 1-11, 13-18, and 20, 22 (and their respective descriptions) show designs and set-ups of implants, and FIGS. 3, 4, 11-16 (and their respective descriptions) show a method and a surgical device for implanting by means of a tensile force being coupled into a tool by which mechanical vibrations are transferred to the implant. In these figures and their descriptions, regions where the implant is to liquefy when the mechanical vibrations act, are pointed out, and in accordance with either aspect or combination of aspects of the invention, such regions may be configured to be (second) regions having material properties rendering them suitable for the liquefaction to start there.

In accordance with any of the aspects or combination of aspects of the invention, the following may hold:

The first and/or the second thermoplastic material portions may be non-resorbable or may be at least partly resorbable. If the primary stability is to be retained, the thermoplastic material is not resorbable or only partly resorbable.

Resorbable polymers are e.g. based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplastics such as for example polyolefins, polyacrylates, polymetacrylates, polycarbonates, polyamides, polyesters, polyurethanes, polysulphones, polyaryl ketones, polyimides, polyphenyl sulphides or liquid crystal polymers (LOPS), polyacetals, halogenated polymers, in particular halogenated polyoelefins, polyphenylene sulphides, polysulphones, polyethers, polypropylene (PP), or corresponding copolymers or blended polymers or composite materials containing the mentioned polymers as components are suitable as non-resorbable polymers.

Specific embodiments of degradable materials are Polylactides like LR706 PLDLLA 70/30, R208 PLDLA 50/50, L210S, and PLLA 100% L, all of Bohringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; the latter has a glass temperature below body temperature); on polydioxanone PDS page 209. Discussion of a further bioresorbable material can for example be found in CA Bailey et al., J Hand Surg [Br] 2006 April; 31(2): 208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene. An overview table of polymers and applications is listed in Wintermantel, page 150; specific examples can be found in Wintermantel page 161 ff. (PE, Hostalen Gur 812, Hochst AG), pages 164 if. (PET) 169ff. (PA, namely PA 6 and PA 66), 171 if. (PTFE), 173 if. (PMMA), 180 (PUR, see table), 186 ff. (PEEK), 189 ff. (PSU), 191 if (POM—Polyacetal, tradenames Delrin, Tenac, has also been used in endoprosthesis by Protec)

The thermoplastic materials may contain foreign phases or compounds serving further functions (if applicable, a light absorbing function as mentioned further above or an even further function combined with a light absorbing function). In particular, the thermoplastic material may be strengthened by admixed fibers or whiskers (e.g. of calcium phosphate ceramics or glasses) and such represent a composite material. The thermoplastic material may further contain components which expand or dissolve (create pores) in situ (e.g. polyesters, polysaccharides, hydrogels, sodium phosphates) or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

For calcium phosphate nanoparticle fillers in degradable polymers see for example Fillers used may include degradable, osseostimulative fillers to be used in degradable polymers, including: β-Tricalciumphosphate (TCP), Hydroxyapatite (HA, <90% crystallinity; or mixtures of TCP, HA, DHCP, Bioglasses (see Wintermantel).

Osseointegration stimulating fillers that are only partially or hardly degradable, for non degradable polymers include: Bioglasses, Hydroxyapatite (>90% cristyllinity), HAPEX®, see SM Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20.

Embodiments of bioactive fillers and their discussion can for example be found in X. Huang and X. Miao, J Biomater App. 2007 April; 21(4):351-74), J A Juhasz et al. Biomaterials, 2004 March; 25(6):949-55.

Particulate filler types include: coarse type: 5-20 µm (contents, preferentially 10-25% by volume), sub-micron (nanofillers as from precipitation, preferentially plate like aspect ratio>10, 10-50 nm, contents 0.5 to 5% by volume)

Potential implant parts not including the thermoplastic material are not resorbable, if the implant is to remain in the human or animal patient's body or if it is to be removed surgically. However, such implant part may also be made at least partly of a resorbable material, which after implantation is gradually replaced by viable tissue.

The plasticizer for all embodiments may be any substance that is suitable of being a plasticizer for the first thermoplastic material. It may comprise one compound or a combination of compounds. It may be liquid, such as a solvent. It may as an alternative be a gas (such as carbon dioxide or solvent vapors, e.g. acetone, tetrahydrofurane, dimethylsufoxide) or a substance that is only activated in situ or shortly before operation, for example by being contained in particles and only released upon activation, or by being grafted molecularly. Activation of such plasticizers may take place by any suitable measures, such as irradiation (for example by UV radiation or microwave energy suitable for breaking bonds and thereby mobilizing the plasticizer).

If the implant comprises porous thermoplastic material, the pores may contain material that can be stimulated by microwaves, such as water, physiological, isotonic solutions like Ringer Lactate, or substances capable of absorbing visible or IR radiation such as higher saturated fatty acids, blood or plasma or plasma replacement substances like plasma expander (such as polysaccharide (Dextran) solutions, glucose solutions). Such stimulatable liquid may be enclosed in closed pores. In case of an open pores material with small pore sizes of smaller than 50 µm, preferably smaller than 5 µm, especially preferred between 0.1 µm and 1 µm, such liquid may be permanently adsorbed in the pores. Before the operation, such a stimulatable liquid may be absorbed by capillary forces if the implant is dipped in the liquid, and then, during or immediately before the operation, may be stimulated by the appropriate radiation. Saturated fatty acids, polysaccharide and/or glucose may also be comprised in the thermoplastic material in the form of particles or molecules.

The invention further relates to a method of fixing an implant within the human or animal body by means of mechanical vibration. This method comprises the steps of providing an implant according to the invention and/or prepared in accordance with a method according to the invention, of bringing the implant in contact with a tissue, of coupling mechanical vibrations into the implant and thereby liquefying material portions of the implant, so that liquefied material interpenetrates structures of the tissue, and of letting the liquefied material re-solidify to thereby establish a connection between the tissue and the implant.

The methods and implants described herein may be used for connecting two parts of the human or animal skeleton or other hard tissue/hard tissue replacement material, or for connecting one part of the skeleton (or other hard tissue/hard tissue replacement material) and a soft tissue part, or for connecting at least one part of the skeleton (or other hard tissue/hard tissue replacement material) and another object. The implants described herein may also be endoprostheses such as e.g. joint prostheses, bone prostheses, intervertebral disc prostheses, artificial ligaments or tendons, artificial teeth, etc. According uses of implants as such are known in the art, and the methods and implants according to the invention may differ from known methods and implants primarily in their structure and in the here-described way the connection to the hard tissue is achieved.

Such applications include the use of an implant/method according to either aspect or combination of aspects according to the invention:

In repair of broken or cut bone: to approximate fragments, reduce and mechanically stabilize fractures Cartilage defect, to replace a joint or a part of a joint (e.g. hip, knee, ankle, foot, hand, finger, wrist, elbow, shoulder)

to attach soft tissues or soft tissue replacements to bone or to other soft tissues to attach membranes, to fix devices with non-orthopedic functions to bone, e.g.

to fix dental implants to fix devices in and on teeth to fix sutures to fix exoprothetic devices, i.e. artificial limps to fix implant parts to each other (see for example PCT/CH 2007/000458)

Alternatively, the methods and implants may also be used for new applications in surgery, some of them being only made possible by the invention according to any one of the above-described aspects.

A category of applications concerns the re-surfacing of joint parts. Examples of re-surfacing techniques have, for example, been described in U.S. provisional patent application No. 60/913,012, that is incorporated herein by reference. According to re-surfacing applications, an element is fixed to remaining bone material by an implant according to any aspect or combination of aspects of the invention. The element may include a coating replacing the cartilage of the joint part, or such a coating may be applied to the element after its fixation.

An other category of applications is the fastening of support elements (such as screws or plates) fixing the relative position of bone fragments after a fracture or after insertion of bone replacement fragments or bone replacement material. Such a support element may, according to the present invention, be fixed, in one or more locations, by an implant according to any aspect or combination of aspects of the invention.

An even further category of applications is the replacement of conventional surgical screws by implants according to any one of the aspects of the invention or according to any combination of aspects.

Yet an other category of applications concerns the anchoring of a suture by means of an implant according to any aspect or combination of aspects of the invention. The suture may be fixed to the implant (or an element fixed by the implant) prior to implantation, by implantation, or it may be fixable to such element after implantation.

Yet a further category is the fastening of a flexible, flat object, such as a tissue or a membrane or the like, to hard tissue/hard tissue replacement material, as described in US 2007-0 265 704, incorporated herein by reference.

BRIEF DESCRIPTION OF THE DRAWINGS

In the following, embodiments of the invention are described with reference to drawings. In the drawings, same numbers designate same elements.

DETAILED DESCRIPTION OF THE INVENTION

Any implant according to the invention and any implant used in a method according to the invention may have an essentially pin-like shape suitable for being introduced in a bore in tissue or any other shape, for example adapted to the shape of a cavity to be filled, or of a tissue part to be replaced, and may further comprise functional elements not shown in the following Figures.

Such functional elements may include fastening means for fastening a further object to the implant. The fastening means may include a simple head-like expansion, form a hook or eye or other element the object may be fastened to, or may include a more sophisticated mechanism such as a thread, a catch, elements of a bayonet mount etc. In addition or as an alternative, the implant or functional element(s) thereof may have a function on their own in the body of the human or animal the implant is used for. For example, the functional elements may be an artificial tooth, a suture anchor or a fracture reduction device or may act as prosthesis etc. In addition or as yet another alternative, the implant may comprise storage means for storing and after implantation slowly releasing a therapeutic agent. Further uses of the implant are possible.

The implant comprises a portion of a thermoplastic material—also called "first thermoplastic material" in this text—which is able to be liquefied by mechanical vibration. The first thermoplastic material preferably at the implantation temperature (assumed to be in the range of a body temperature of around 37° C. in the following) has a modulus of elasticity of 0.5 GPa or more and preferably is below the glass transition point. The implant may further comprise regions of not liquefiable material such as a 'hard core', i.e. a core of a material with less elasticity than the first thermoplastic material, such as a metal like Titanium.

The first thermoplastic material may be any material suitable for being liquefied by mechanical vibration and further suitable for being introduced in a human or animal body. For example, the first thermoplastic material may be a polylactide such as any one of the products LR708 (amorphous Poly-L-DL lactide 70/30), L209 or L210S by Bohringer Ingelheim or a polycarbonate or any other suited polymer, for example, of the group mentioned further above in this text.

The implant comprises a surface region suitable to be coupled to a sonotrode of a device by which mechanical vibrations are coupled into the implant.

The implant may further comprise structural and/or other means enhancing osseointegration (secondary stability).

Concerning designs and uses of implants, reference is made to the disclosures of the publications WO 02/069 817, WO 2004/017 857, WO05079696, and WO05105208, as well as to the U.S. provisional applications 60/826,296 (corresponding to PCT/CH 2007/000458), 60/744,167 (corresponding to US 2007-0 265 704), 60/826,300, and 60/913,012, which are all incorporated herein by reference.

Figure 1A:
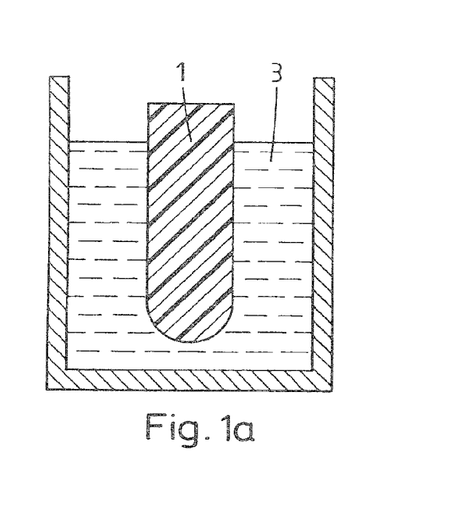
FIG. 1a shows, as a stage of a method of preparing an implant, an implant dipped into a solvent.

The implant 1 shown in section in FIG. 1a has a pin-like structure and is made of the first thermoplastic material. Like in all Figures—unless explicitly stated otherwise—the implant is shown in an upright orientation, i.e. the implant is illustrated with the proximal end above the distal end, so that an implantation direction with respect to the implant is downward.

In order to modify a material portion in the vicinity of the implant surface to be softened, the implant is dipped into a solvent 3 serving as plasticizer. The solvent may comprise any compound suitable to act as plasticizer for the first thermoplastic material. For example, for many thermoplastic materials including polylactides (e.g. poly-L-lactice (like L210S from Böhringer Ingelheim), suitable solvents are tetrahydofuran (THF), acetone, ethanol or other alcohols, or n-Pyrrolidone, dimethylene disulfoxide (DMSO). The skilled person will know many further suitable solvents, including, for certain polymers, water. In the following text, the treatment of material portions, situated in the vicinity of surface regions of the implant and consisting of the first thermoplastic material, by dipping the implant into a solvent is called "surface treatment". The surface treatment may take place at room temperature, at a temperature in the region of the implantation temperature, or at any other temperature suitable for carrying out a controlled solvent absorption process. The surface treatment may comprise two sub-steps:

Bringing surface regions (the surface regions may make up the entire implant surface, but preferably without the surface through which the mechanical vibrations are to be coupled into the implant) of the first thermoplastic material in contact with a solvent and keeping it in contact with the solvent at a first temperature and for a first period of time.

After separation from the solvent and before implantation, waiting for a second period of time at a second temperature.

The first and second temperatures may, but need not be identical. The second sub-step is optional. During the second sub-step, the implant may be in contact with an other liquid material—it may for example be dipped in water—or may be exposed to air, a noble gas, or an other gas mixture.

Portions of the first thermoplastic material become plasticized material portions 1.1 (also called "second material portions" in this text) due to the solvent molecules which diffuse into the first thermoplastic material.

Figure 1B:
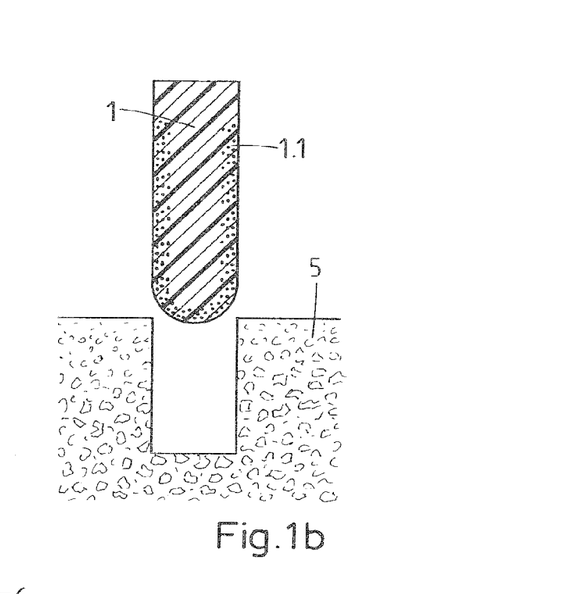
FIG. 1b shows the implant of FIG. 1a, after the step of dipping and before implantation.
Figure 1C:
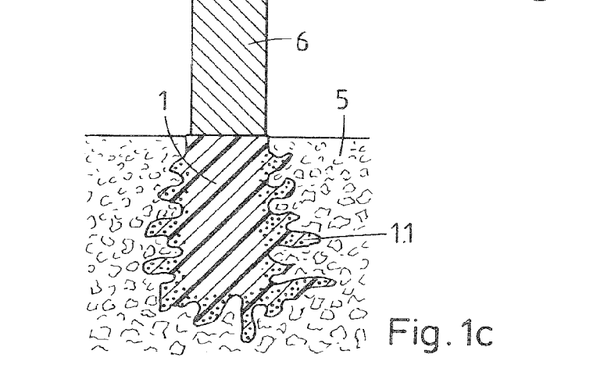
FIG. 1c shows the implant of FIGS. 1a and 1b during implantation.

Thereafter, the implant 1 with the plasiticized material portions 1.1 is implanted, for example in bone material. To this end, as shown in FIG. 1 b, a pre-drilled hole in the bone tissue 5 may be provided. As an alternative, the implant may be inserted in a pre-existing cavity of the bone tissue or may be inserted by being pressed onto an (even) surface of the bone tissue which has not been treated or from which merely the periosteum and possibly the corticalis has locally been removed. As schematically illustrated in FIG. 1 c, implantation is accomplished by pressing the implant against the tissue and at the same time impinging it with mechanical vibrations transmitted by a sonotrode 6. By this, portions of the thermoplastic material liquefy and are pressed into pores and/or other surface structures in the tissue. Such pores and/or other surface structures in the tissue may be pre-existing (bone tissue generally comprises a porous structure, especially, of course, spongy bone) or may be created during implantation by the pressure applied. After the mechanical vibrations stop, the material re-solidifies and forms a connection to the tissue with a high primary stability.

Thereafter, the plasticizer molecules may diffuse out of the thermoplastic material to be resorbed (e.g. metabolized) and/or excreted by the organism of the patient. This effect enhances the mechanical stability of the thermoplastic material in the region of interpenetration of the tissue and thus adds to the strength of the connection.

The softened material portions have the following effect: Due to their being, at the implantation temperature of e.g. 37° C., above the glass transition temperature, they absorb, according to the principle explained above, more mechanical energy per volume than the first thermoplastic material without the plasticizer. Therefore, the heating effect at the periphery, where the material is softened, is locally stronger than in a central region. As a consequence, the softened material is liquefied more easily and already at a lower contact pressure to the bone tissue than it would be in the case for implants according to the prior art. This softened material may therefore enter into pores and/or other structures of the tissue more easily. A second effect is that the softened material, by absorbing more mechanical energy also heats up neighboring material portions of the not (or less) softened first thermoplastic material. By this, such neighboring material portions are themselves brought above their glass transition temperature of more than 37° C. and thereafter contribute to the enhanced absorption effect. The softened surface portions therefore even have an effect if their volume is comparably small—they act in the manner of a catalyst helping the enhanced absorption effect in not softened material portions to start. The not softened material portions therefore also enter into pores and/or other structures more easily.

Experimental Examples

The following experimental examples were carried out using pin-shaped implants of 3.5 mm diameter. The implantation was carried out using the Branson E-150 ultrasonic device, sonotrode 3.5×12.5 with o-ring no. 9.

A pin-shaped implant of LR708 (PLDLLA 70/30; Boehringer Ingelheim) is dipped in THF at room temperature during one minute. Thereafter, the implant is directly inserted (no second sub-step) in open cell 5.5 sawbone material (which in the examples serves as model tissue modeling bone tissue). An interpenetration of the pore structure which is enhanced compared to the not surface treated implant can be observed.

Like example 1 but the implant is inserted 30 min. or 90 min. after having been exposed to the solvent (second time period=30 or 90 min). The interpenetration is further enhanced compared to example 1.

Like example 1 or 2 but the implant is exposed to the solvent for 5 min or 10 sec.

Like example 1, 2 or 3, but the implant is implanted in a pig's femoral condyle. Also in this system, an enhanced interpenetration can be observed, especially in a region around the distal end of the implant.

Like example 4 but the implant is made of Polycarbonate, L209, or L210S.

According experiments with L209 (PLLA; Boehringer Ingelheim), L210S (PLLA; Boehringer Ingelheim), and Polycarbonate were carried out; for polycarbonate also an effect of the solvent treatment was observed, whereas for the PLLA a weaker or no effect of the solvent treatment was tangible.

As an alternative, the implant may be of a material as for examples 1 to 5 and the treatment the same as for any one of examples 1 to 5 but the solvent is n-Pyrrolidone. This solvent is reputed to support tissue regeneration. A system for guided tissue regeneration GTR™ and guided bone tissue regeneration GBR™ by Inion makes use of this fact. The named system is a Biodegradable Membrane Systems based on Polylactic Acids (PLA), PDLA, PGA (Polyglycolide), TMC (Trimethylene Carbonate), and co-polymers of polylactic and polyglycolic acids (PLGA).

Further, especially suited solvents are acetone or dimethylene sulfoxide (DMSO), which both have the advantage of having an acceptable biocompatibility (thus sufficiently low toxicity)). When one of these solvents is used, direct contact to the solvent is required, the solvent could also be absorbed in its gas phase, to allow a better control of solvent penetration, since absorbtion activity is directly proportional to the vapor pressure of the solvent present.

Whereas the embodiment of FIG. 1$a$ through 1$c$ is based on a local plasticizing process to be carried out more or less shortly before operation, other embodiments may be envisaged, and they are described referring to the following Figures.

The surface treatment enhances the interpenetration compared to the untreated implant in all examples. Exposure to the solvent at room temperature for more than one minute does not seem to enhance the effect for the observed system, but of course for each system the optimum parameters can be determined individually.

Figure 2:
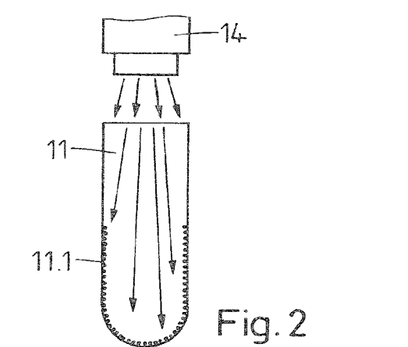
FIG. 2 illustrates an alternative method of preparing an implant before or during implantation.
Figure 11:
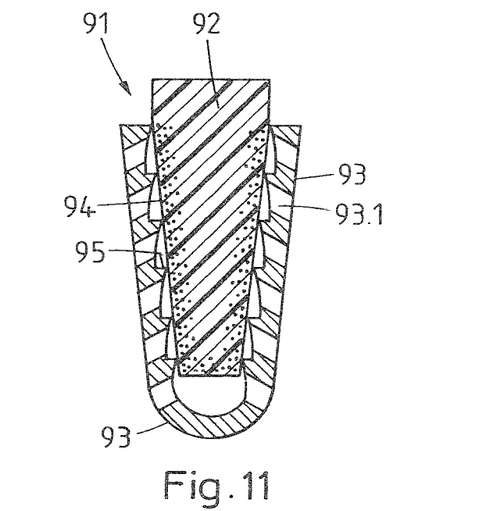
FIG. 11 illustrates another example of an implant according to the invention.

The implant 11 shown in FIG. 2 is essentially transparent for electromagnetic radiation of a certain wavelength range (such as for infrared and/or visible radiation emitted by a light source 14) and comprises, along a surface, an absorber 11.1. In the drawing, the absorber is depicted to be particulate, i.e. to comprise a plurality of particles (e.g. pigment) arranged in the vicinity of the implant surface. The absorber may also be a molecular light absorbing substance or it may constitute a further body arranged at the surface of the transparent body such as e.g. a sleeve as shown in FIG. 11 made e.g. of a metal. In a central region, the implant is essentially non-absorbing for radiation of the wavelength range. As illustrated by the arrows in FIG. 2, the central, non-absorbent region of the implant is capable of directing radiation that is proximally coupled in to the peripheral region where the absorber is located. Suitable light absorbing substances as mentioned further above are e.g. saturated fatty acids, polysaccharides, glucose, calcium phosphates (TCP, HA, DHCP), sodium phosphates, calcium carbonates.

In addition or as an alternative to the absorption of visible light by a light absorbing substance, the implant may also comprise porous thermoplastic material portions, where the pores contain a material capable of absorbing light energy, as previously mentioned.

For bringing the surface region portions above the glass transition temperature for coupling in mechanical vibrations, shortly before implantation, when the implant is positioned, electromagnetic radiation, e.g. laser light (plasticizing agent) is coupled into the implant, and thereby the surface region comprising the absorber is locally heated to a temperature above the glass transition temperature. When the implant is in contact or is brought into contact with the tissue, the temperature relaxes comparably quickly after the radiation has stopped (plasticizing agent is removed). However, at least one of the two following measures may be taken so that nevertheless there are thermoplastic material portions above the glass transition temperature when the mechanical vibrations start impinging:

High operation speed: The mechanical vibrations start before the implant surface has cooled to below the glass transition temperature;

Kinetic blocking: In some polymer systems, especially amorphous systems like for example R208 (PDLLA of Bohringer Ingelheim), the material after a quick cooling to below the reported glass transition temperature is still above the glass transition point for some time.

As a further measure, the absorber may be placed somewhat (for example by between 0.1 mm and 0.5 mm) underneath the surface, so that the hottest place is not in immediate contact with the tissue.

The implant depicted in FIG. 2 may, as an alternative to the described process that comprises melting in two steps (firstly by absorption of electromagnetic radiation energy by the absorber, then by absorption of mechanical energy) also be liquefied in a single step. In this, the electromagnetic radiation—that, in all embodiments including irradiating, may be laser radiation—is coupled into the implant with an intensity and duration sufficient to bring the surface region that comprises the absorbent above the melting temperature. If the implant, at the time when the surface regions are melted, is slightly pressed towards the distal side, an anchoring process that includes interpenetrations of surface unevenness, openings, inhomogeneities or the like may occur also absent any mechanical vibrations. After thermoplastic material of the surface region has liquefied and interpenetrated the tissue in which the implant is to be anchored, the radiation may be stopped, and the thermoplastic material re-solidifies to provide an anchor. The overall heat impact on the tissue in this may be kept low because, like in the case of liquefying by mechanical oscillation, the liquefaction takes place only locally in the surface region, and not the whole implant is heated.

Figure 3:
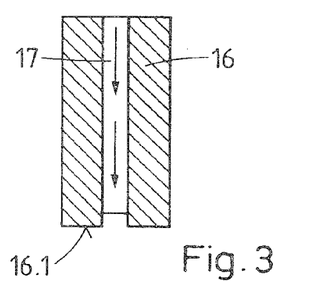
FIG. 3 shows a sonotrode for preparing an implant before or during implantation.

In addition or as yet another alternative, the local heating may take place while the mechanical vibrations impinge, at least in the beginning of their action. FIG. 3 very schematically shows a sonotrode 16 which makes this possible. The sonotrode comprises an integrated optical waveguide 17. Electromagnetic radiation may be guided through the waveguide and coupled into the implant while the mechanical vibrations are coupled into the implant by means of a ring shaped outcoupling face 16.1.

Other measures of locally heating portions of an otherwise homogeneous or of an inhomogeneous first polymer region to a temperature above the glass transition temperature may be envisaged. Such measures include heating by irradiating from an outside, by baking, or by dipping into a bath of a hot liquid before implantation. In principle, also heating by microwaves, inductive heating etc. may be envisaged. Such heating may be promoted by local inhomogeneities of the first thermoplastic material, such as by polar molecules arranged primarily in the vicinity of a surface region etc. As mentioned above for the heating through light absorption, also the further heating methods may be used for melting a desired amount of the thermoplastic material without additional application of vibratory energy.

Figures 4, 6:
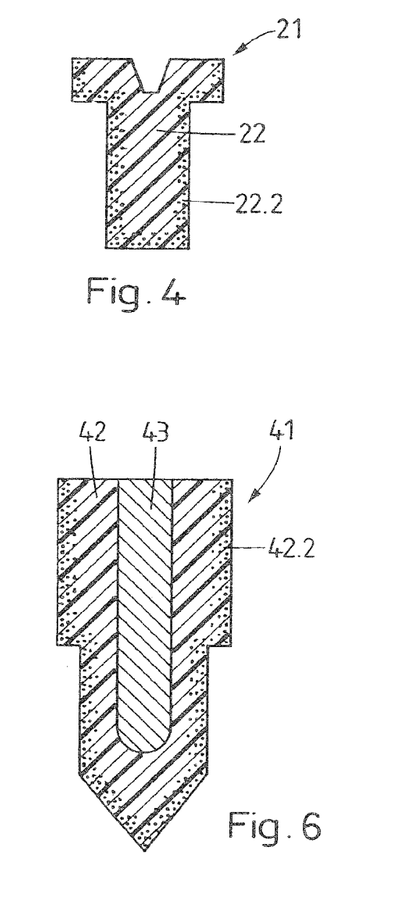
FIG. 4 shows an embodiment of an implant.
FIG. 6 shows another variation of an implant.

Yet an other variant is—also very schematically—depicted in section in FIG. 4. The implant 21 is essentially made of a homogeneous thermoplastic material 22, but includes material portions 22.2 where the thermoplastic material has been modified to have a lower glass transition temperature.

A first example of such modification would be the above-described exposure to and therewith absorption of a plasticizer. When the modification, at room temperature, is to be stably confined to certain portions in a vicinity of the implant surface only, the plasticizer has to be of comparably reduced mobility. For example, the plasticizer may diffuse in the polymer at an elevated temperature only, so that the implant has to be pre-treated at an elevated temperature and thereafter may be brought on the market in the surface treated form.

A second example of such modification is a surface treatment by exposure to radiation with limited penetration depth in the thermoplastic material, such as radiation by electron beam or ion beam. In this case, such radiation may be such as to reduce the local molecular weight or generate lower molecular weight components in the polymer that act as internal plasticizer. Such effects can be temporal since radiation induced chain scission—e.g. by radical formation—can be active for quite some time, allowing the polymer to repolymerize/cross-link after implantation. Therefore, as in previously mentioned cases, also a thermosetting material could also be applied as this second material.

Figures 5, 7:
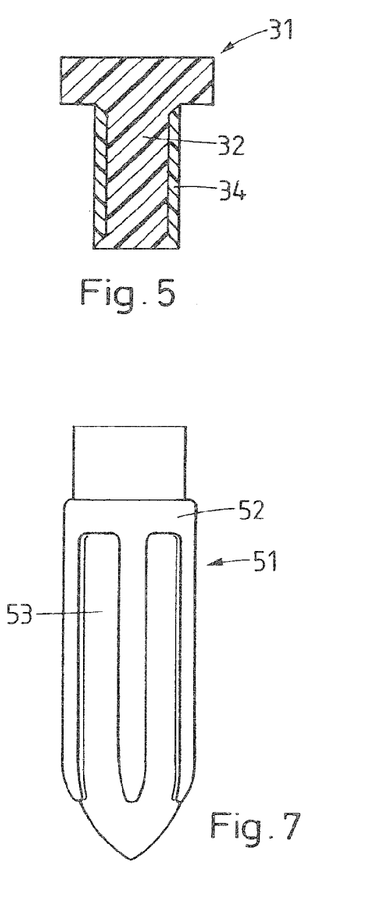
FIG. 5 shows a variation of an implant.
FIG. 7 shows another variation of an implant.

In FIG. 5, yet another embodiment of an implant 31 according to the invention is depicted in section. The implant comprises a central body 32 of a first thermoplastic material and a peripheral portion 34 of a second thermoplastic material. The second thermoplastic material is arranged at locations where the implant is to interpenetrate structures of a tissue it rests against and has a glass transition temperature which is below 37° C. An example of such a second thermoplastic material is polycaprolactone or a mixture of polycaprolactone with another material. A further example is a thermoplastic (such as the first thermoplastic material) comprising a polymeric plasticizer. Examples of such polymeric plasticizers are polycaprolactone, polyacrylate, and gutta-percha. The skilled person will know other examples of thermoplastic materials with a glass transition temperature below about 37° C. The thickness of the second thermoplastic material 34 may be between 0.1 mm and 0.5 mm.

An implant as illustrated in FIG. 5 and comprising a peripheral portion made e.g. of gutta-percha is applicable not only as an implant in the proper sense of the word, but also as a plug for sealing the root of a tooth, i.e. to be connected to the inner dentine surface of a viable tooth.

As an alternative to being applied as coating, the second thermoplastic material portions 34, which at least during implantation have thermoplastic properties, can be applied as vesicles, or as blended component close to the surface layer.

In case the second material portions—being thermoplastic at least during implantation—are such as to cross-link after implantation, the kinetics of the cross-linking process has to be significantly slower (with a time constant of at least a factor 2, preferably at least a factor 5 higher) than the time required for insertion.

FIG. 6 shows an implant 41 that has been produced according to the principles described referring to FIGS. 1a through 1c or FIG. 4. In contrast thereto, however, the implant 41 comprises a core 43 of a material that is not liquefiable by mechanic vibrations under implantation conditions, for example of a metal (like titanium (Grade 1-5), titanium alloys (e.g. TiALV64, TiAlNb711; see also Wintermantel, chapter 10.7, p. 144ff.), cobalt based alloys (see for example Wintermantel chapter 10.6, p. 140 ff., especially table 10.8), stainless steel (see for example Wintermantel chapter 10.5, p. 137 ff.; table 10.5), Magensium alloys (see for example M P Staiger et al. Biomaterials 2006 March; 27(9):1728-34, for Mg—Ca alloys see for example Z. Li, X. Gu, Y. Sheng in Biomaterials 2008 Jan. 10), Tantal or Zirconium alloys (e.g. Oxinium® from Smith & Nephew), a ceramic (like a Zirconium oxide (Wintermantel chapter 12.2, p. 214 ff. or Aluminum oxide (Wintermantel chapter 12.1, p. 212 ff.), nanocristalline hydroxyapatite (e.g. Nanoapatite from Angstrom Medical Inc. MA, USA), a thermosetting polymer, or a thermoplastic with a melting temperature above e.g. 100° C. The first polymer 42 with the modified portions 42.2 in the vicinity of a surface region is arranged around the core.

The core 43 enhances the mechanical stiffness of the implant. In addition, it furthers the energy transfer—by way of mechanical vibrations—to the distal end of the implant and thus reduces energy absorption in a central region of the implant.

In the embodiment according to FIG. 6, the first thermoplastic material (including the surface treated portions thereof) forms the entire portion of the surface to be in contact with the tissue in which the implant is implanted. An implant in which the first thermoplastic material does not form the entire contact surface is shown in FIG. 7. The implant 51 according to FIG. 7 comprises first surface regions formed by the hard (i.e. not liquefiable under implantation conditions) material 53 and second surface regions formed by the surface treated first thermoplastic material 52.

Figure 8:
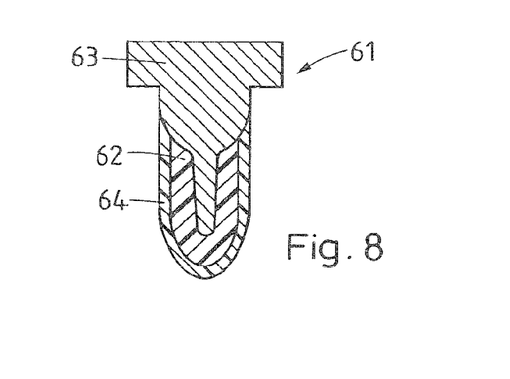
FIG. 8 shows yet another variation of an implant.

Yet another variant is depicted in section in FIG. 8, where the implant 61 comprises a core 63 of a material not liquefiable under implantation conditions, material portions of a first thermoplastic material 62 with a glass transition temperature around or above 37° C., and material portions 64 of a second thermoplastic material.

In a combination of the teachings of FIG. 7 and FIG. 8, the thermoplastic material partially forming the surface of the implant of FIG. 7 may consist of two layers, one having a glass transition temperature above the implantation temperature (preferably the layer beneath a surface layer), and one having a glass transition temperature below the glass implantation temperature (preferably the surface layer).

Figure 9:
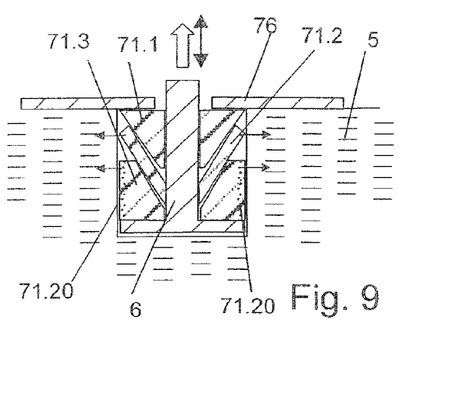
FIG. 9 shows yet another variation of an implant.

FIG. 9 depicts an embodiment which is based on the principle that it is compressible in the direction of a compression axis under local enlargement of a distance between a peripheral surface of the implant and the compression axis, wherein compression is effected between a vibrating tool (sonotrode 6) and a counter-element 76. By this, coupling of mechanical vibrations into the implant and excerpting of a force on the tissue surface is possible even if no or very little force is excerpted on the base of the bore in the bone tissue 5. This principle has been described in the provisional U.S. patent application 60/826,300. It is therefore especially suited for implantation in bone tissue that is osteoporotic or otherwise unsuitable for counteracting large forces, and thus the combination with the approach according to the invention is especially advantageous. The implant 71 depicted in FIG. 9 comprises three implant components 71.1, 71.2, 71.3 which are able to be shifted relative to one another, whereby the implant radius increases. In the shown embodiment, the sonotrode 6 acts on the implant in a direction pulling the implant out of the bore, the counter-element 76 counteracts the action of the sonotrode and prevents the implant from being pulled out of the bore.

An implant 71 of the kind depicted in FIG. 9 may be surface treated or provided with a second thermoplastic material in peripheral regions only or on the entire surface. In FIG. 7, surface treated material portions 71.20—represented by a dotted area—are only shown along the periphery.

In the embodiments of FIGS. 1a-1c, FIG. 4, FIG. 6, or FIG. 7 the plasiticizer may be—and preferably is—resorbable or excretable. Resorbable plasticizers include THF, Acetone, Alcohols, n-Pyrrolidone and others. As far as they refer to plasticizers able to be removed after implantation (diffusion and resorption or excretion), the embodiments of the named Figures correspond to both, the first and the second aspect of the invention.

Figure 10A:
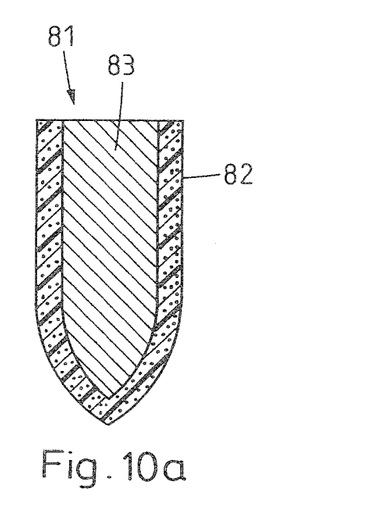
FIG. 10a shows an implant, before implantation, the implant comprising a hard core and a plasticized thermoplastic material shell.
Figure 10B:
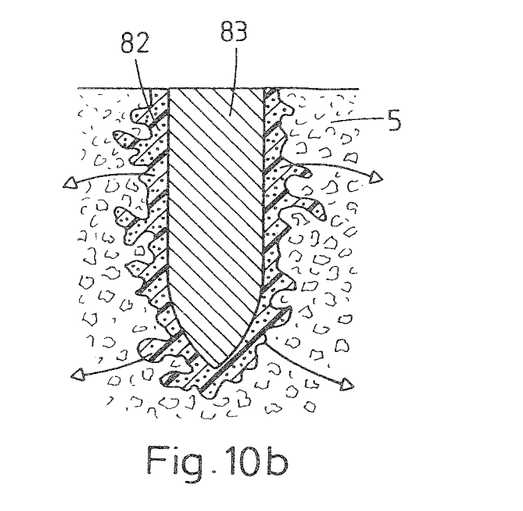
FIG. 10b shows the implant of FIG. 10a, after implantation.

An example of a further implant that corresponds to the second aspect of the invention is depicted in FIG. 10a. The implant comprises a core 83 of a material not liquefiable under implantation conditions, for example of titanium or a ceramic or a thermosetting polymer. The core 83 is coated, at least in some regions, by a (second) thermoplastic material 82. The thermoplastic material 82 comprises a polymer and a plasticizer. The glass transition temperature of the second thermoplastic material 82 is below about 37° C. but would be above 37° C. in absence of the plasticizer. After implantation (FIG. 10c), the plasticizer diffuses out and is resorbed or excreted, as illustrated by the arrows. As a consequence, the thermoplastic material interpenetrating pores and/or other surface structures in the bone tissue 5 hardens after implantation.

The implant as depicted in FIGS. 10a and 10b can also be pretreated with a platicizing agent in the form of radiation energy (e.g. visible or infrared light) which is coupled into the transparent thermoplastic material of the implant and is absorbed by the surface of the core 83 and therewith either heats the thermoplastic material to above its glass transition temperature or even melts it for implantation without vibrational energy.

An exemplary representative of a further category of implants is depicted in FIG. 11. Also this implant 91—like all previously shown implants—is illustrated as having a pin-like shape but may have any other shape. In addition to material portions of thermoplastic material, the implant comprises a sleeve 93 of a material which is preferably not liquefiable by mechanical vibrations under implantation conditions, for example of metal, ceramic, glass, a thermosetting polymer or a thermoplastic polymer having a high glass transition temperature of, for example, more than 150° C., or of a corresponding composite material. The material to be liquefied is arranged within the sleeve.

The sleeve 93 is provided with openings 93.1 arranged in places where anchoring in the tissue is desired and dimensioned such that liquefied material can be pressed through the openings. Such an embodiment of the implant is suitable for example for the application of thermoplastic material that cannot withstand the mechanical loading caused by the resonator pressing on the implant or for applications where a good confinement of the anchoring locations and/or of the thermoplastic material is desired or necessary.

In addition to the sleeve 93 comprising the openings 93.1 at well defined locations (as illustrated in FIG. 11) or as an alternative thereto, the sleeve 93 may, in accordance with a special embodiment, also comprise a porous sintered material.

For implantation, the implant with a sleeve 93 is positioned in a tissue opening and the mechanical vibrations are applied to the thermoplastic material arranged in the interior of the sleeve such that the thermoplastic material is at least partly liquefied and pressed out of the opening and into the surrounding tissue. Obviously, liquefaction in this particular case starts due to friction between the thermoplastic material and the inside surface of the sleeve, for which preferably energy directing elements in the form of e.g. sharp edges 95 on the sleeve inside surface in the region of the openings are provided.

During implantation, the sleeve 93 may be held against a tool that applies the mechanical vibrations not only by the base of the opening—for example if such base is not suitable of being loaded mechanically—but also by being actively held or by comprising a flange protruding sideways at the proximal end of the sleeve, so that the flange may prop on a stable surface of the tissue. In accordance with the first aspect of the invention, the implant 91 of FIG. 11 comprises first thermoplastic material portions 92 and second thermoplastic material portions 94. The second thermoplastic material portions are arranged in locations in which material is to be liquefied, i.e. near the openings and/or in the vicinity of the energy directing elements. Other arrangements may be envisaged, for example with the second thermoplastic material portions 94 covering surface regions of the first thermoplastic material portions also in regions where no openings 93.1 are present, or with the second thermoplastic material portions filling the openings 93.1 at least partially, potentially protruding into an interior of the first thermoplastic material portions. In such embodiments it is possible for the sleeve to comprise a material which is liquefiable under implantation conditions, e.g. the first thermoplastic material.

In the embodiment as shown in FIG. 11, the second thermoplastic material portions 94 cover about the whole surface of the first material 92. This can be achieved by a corresponding surface treatment of the first material 92 before it is introduced into the sleeve 93. If the second material portions are to be arranged only near the openings 93.1 in the sleeve, this may for example be achieved by treating the whole implant (including sleeve) in the manner described referring to FIG. 1a or FIG. 4. If the implant is treated by being dipped into a solvent acting as plasticizer, the dimensions of the openings in the sleeve, the surface tension of the solvent and the surface properties of the sleeve material are to be matched such that the solvent is able to penetrate into the openings 93.1 in the sleeve.

The plasticizer causing the glass transition temperature of the second thermoplastic material portions to be below the implantation temperature is preferably to diffuse out of the implant material after implantation, and to be resorbed and/or excreted.

As an alternative to the embodiment illustrated in FIG. 11, the second thermoplastic material portions may also be of a different polymeric composition than the first thermoplastic material portions, similar to the embodiments illustrated in FIG. 5 and FIG. 8.

Pretreatment of the embodiment according to FIG. 11 may also comprise use of a platicizing agent in form of thermal energy, which is produced by absorbing radiation (preferably visible or infrared light) coupled into the transparent first material at the inside surface of the sleeve and therewith heat the surface of the first material above its glass transition temperature or even melt it so as to be pressed out of the sleeve without application of vibrational energy.

As yet another alternative, an implant according to the second aspect of the invention may also be formed as a sleeve-like element with openings containing the thermoplastic material portions inside, wherein all the thermoplastic material in the sleeve may have the characteristics of the second material portions described for other embodiments.

As for all embodiments of both aspects of the invention, the thermoplastic material portions, especially the second thermoplastic material portions need not be (but preferably are) a thermoplastic material in a general sense but may as an alternative exhibit thermoplastic properties only temporarily during implantation, and may for example thereafter be cured to yield a cross-linked, non-thermoplastic material. Curing may take place by any known curing method, for example induced by the heat present during implantation, by radiation, or by being kept for some time at body temperature etc.

Features of the different embodiments as described above may be combined.

In all embodiments, the portions of the surface treated first thermoplastic material and/or the surface portions of the second thermoplastic material may be located according to specific needs. For example, as shown in FIG. 5, these surface portions may be arranged along a circumferential surface only if the connection to the tissue is to be made primarily along the circumferential surface and not at the distal end. Other specific layouts are possible.

Figure 12:
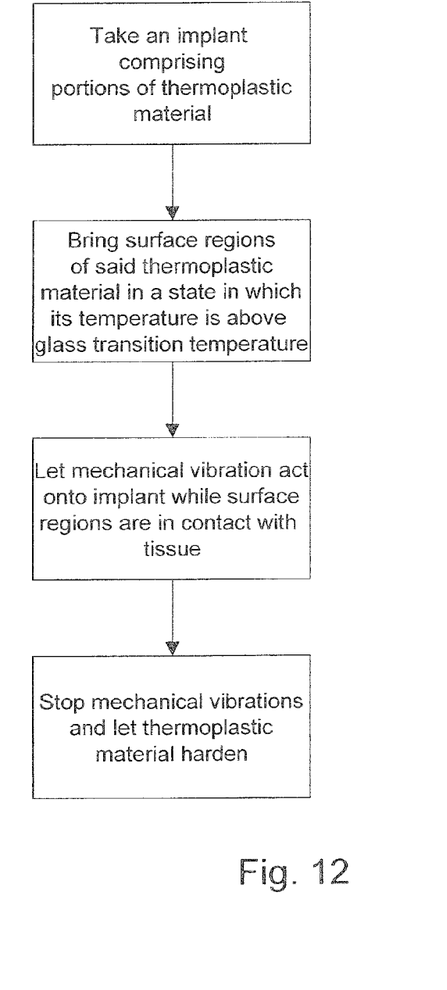
FIG. 12 is a flowchart showing method steps of the method according to the invention.

FIG. 12 shows a flowchart representing method steps of a method of preparing an implant and implanting it in human or animal tissue, especially bone tissue.

Figure 13:
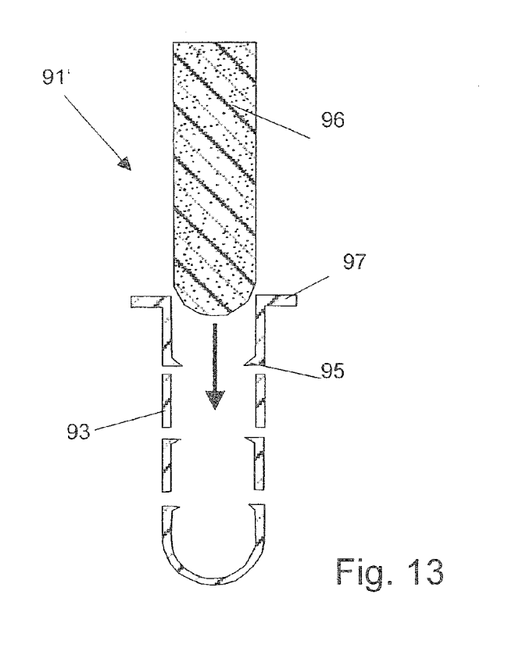
FIG. 13 illustrates yet another example of an implant according to the invention.

FIG. 13 depicts a variant of the implant shown in FIG. 11. Also the implant 91' of FIG. 13 comprises a sleeve 93 with a plurality of openings 93.1. The sleeve is dimensioned to receive an element 96 of thermoplastic material. In contrast to the implant 91 of FIG. 11, however, the implant 91' of FIG. 13 is of a thermoplastic material and itself constitutes the first thermoplastic material portions or a part thereof. The element 96 may comprise, at least on regions, a thermoplastic material different from the first thermoplastic material and constituting the second thermoplastic material. As an alternative, as illustrated in FIG. 13, it may be of a same polymeric composition as the first thermoplastic material, but in addition may comprise a plasticizer at least in regions. As in the above-mentioned embodiments, the plasticizer may be applied by a treatment as described referring to FIG. 1a or FIG. 4.

The implant shown in FIG. 13 comprises an—optional—flange 97 protruding sideways near to the proximal end of the sleeve 93.

When, during implantation, the mechanical vibrations start to act, the thermoplastic material is caused to liquefy. Therein, first the second thermoplastic material of the element 96 starts being liquefied, especially in the regions close to the sharp edges 95. During the implantation process, also thermoplastic material of the sleeve 93 may start being liquefied, by indirect heating (i.e. by absorbing heat generated in the second thermoplastic material) or by direct heating, due to absorption of mechanical energy.

The embodiment of FIG. 13 is especially advantageous in cases where either the locations where liquefied material is to penetrate into the tissue should be well-defined or the tissue itself is not capable of accepting high mechanical loads and where a, for example, metallic sleeve or other counter element is not desired.

Figure 14:
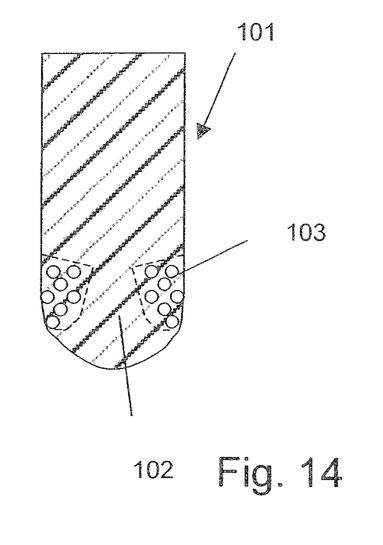
FIG. 14 shows an implant according to the third aspect of the invention.

In FIG. 14—referring to a simple example of a one-material-pin-shaped implant 101—the third aspect of the invention is illustrated. The implant 101 comprises first regions 102 of a thermoplastic material and comprises second regions 103 of a thermoplastic material, where the thermoplastic material of the second regions 103 is a thermoplastic foam (schematically illustrated to have closed pores of approximately same sizes; it could equally well comprise pores of different sizes and/or open pores). In the illustrated embodiment the first regions 102 and the second regions 103 comprise a same thermoplastic material, but this is not necessary.

Figure 15:
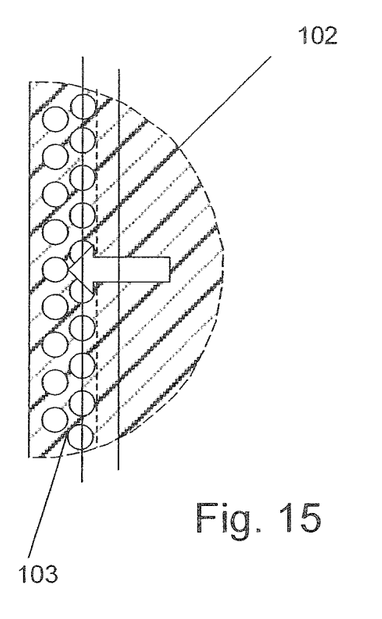
FIG. 15 illustrates a principle of the third aspect of the invention.

FIG. 15, finally illustrates the principle of the third aspect of the invention. The energy of mechanical vibrations that are being propagated from the first region to the second region, is concentrated on a comparably smaller cross section. Since the energy is conserved at the transition from the first to the second region, the power per cross section area of the vibrations is amplified, so that heating in the material portions between the pores is more efficient than in the "bulk" of the first region. The two vertical lines in FIG. 15 illustrate cross sectional areas in the first and the second region, respectively; it is clear from the figure that the actual material cross section in the first region is larger than in the second region.

Various other embodiments may be envisaged without departing from the scope and spirit of the invention.

What is claimed is:

1. A method of implanting an implant in human or animal tissue, comprising the steps of:
   providing the implant, the implant comprising an implant body with a central region forming a core of the implant body and a peripheral region, the central region comprising material transparent for electromagnetic radiation of a spectral range belonging to at least one of the infrared part of the optical spectrum and of the visible part of the optical spectrum, the peripheral region comprising a thermoplastic material and an absorber comprising a material that is different from the thermoplastic material, the absorber being capable of absorbing electromagnetic radiation of said spectral range;
   coupling electromagnetic radiation that includes radiation within said spectral range into the implant body from the proximal end thereof, the electromagnetic radiation being conducted through the central region and being at least partially absorbed by the absorber;
   causing thermoplastic material portions in the peripheral region to be liquefied, and pressing the liquefied thermoplastic material portions into at least one of surface unevenness, pores, and of surface inhomogeneities of the tissue; and
   letting the thermoplastic material portions re-solidify to yield an anchor of the implant.

2. The method according to claim 1 wherein the step of causing the thermoplastic material portions in the peripheral region to be liquefied comprises coupling mechanical vibrations into the implant while the peripheral region is in contact with tissue.

3. The method according to claim 1, wherein the step of causing the thermoplastic material portions in the peripheral region to be liquefied comprises coupling the electromagnetic radiation into the implant body from the proximal end thereof with an intensity and duration sufficient to cause the material portions to be liquefied due to the impact of heat generated by the absorption.

4. The method according to claim 1, comprising the additional steps of:
   providing a bore in the tissue; and
   placing the implant in the bore;
   these additional steps being carried out prior to the step of causing the thermoplastic material portions to be liquefied.

5. The method according to claim 4, wherein at an onset of the step of causing the thermoplastic material portions to be liquefied, the thermoplastic material portions are arranged in a vicinity of the at least one opening.

6. The method according to claim 1, wherein coupling the electromagnetic radiation into the implant body comprises coupling a tool with an integrated optical waveguide to the implant body and guiding the electromagnetic radiation through the waveguide.

7. The method according to claim 1, wherein the electromagnetic radiation is laser radiation.

8. The method according to claim 1, wherein the peripheral region comprises a sleeve of a material that is not transparent for the electromagnetic radiation.

9. The method according to claim 8, wherein the sleeve comprises a material which is not liquefiable by mechanical vibration.

10. The method according to claim 1, wherein the absorber comprises at least one of a saturated fatty acid, polysaccharide, glucose, calcium phosphate, sodium phosphate, calcium carbonate.

11. The method according to claim 1, wherein the absorber is particulate or molecular.

12. The method according to claim 1, wherein the absorber is an absorbing body.

13. The method according to claim 1, wherein the absorber is integrated in the thermoplastic material portions of the peripheral region.

14. The method according to claim 1, wherein the absorber is in immediate contact with the thermoplastic material portions of the peripheral region.

15. The method according to claim 1, wherein the transparent material of the central region and the thermoplastic material portions are arranged adjacent to each other.

16. The method according to claim 15, wherein the thermoplastic material portions are resorbable.

17. The method according to claim 1, wherein the central region is contiguous with the peripheral region and is of a same material, except for the absorber of the peripheral region.

18. The method according to claim 1, wherein the implant extends in an elongate manner between a proximal end and a distal end.

19. A method of implanting an implant in human or animal tissue, comprising the steps of:
   providing the implant, the implant being elongate and comprising an implant body extending between a proximal end and a distal end, the implant body comprising a central region and a peripheral region, the central region comprising material transparent for electromagnetic radiation of a spectral range belonging to at least one of the infrared part of the optical spectrum and of the visible part of the optical spectrum, the peripheral region comprising a thermoplastic material and an absorber comprising a material that is different from the thermoplastic material, the absorber being capable of absorbing electromagnetic radiation of said spectral range;
   providing an opening in the tissue,
   placing the implant in the opening,
   while the implant is placed in the opening, using a waveguide to couple electromagnetic radiation from the proximal end of the implant into the central region of the implant body, the radiation including radiation within said spectral range from the proximal end thereof, until the peripheral region is heated due to the electromagnetic radiation being absorbed by the absorber;
   causing thermoplastic material portions in the peripheral region to be liquefied, and pressing the liquefied thermoplastic material portions into at least one of surface unevenness, pores, and of surface inhomogeneities of the tissue surrounding the opening; and
   letting the thermoplastic material portions re-solidify to yield an anchor of the implant.

* * * * *